(12) United States Patent
Besing

(10) Patent No.: US 7,452,324 B2
(45) Date of Patent: Nov. 18, 2008

(54) RADIATION SHIELD FOR A SAFETY SYRINGE HAVING A NEEDLE SHEATH

(75) Inventor: Quent Besing, Eureka, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 676 days.

(21) Appl. No.: 10/551,119

(22) PCT Filed: Apr. 8, 2004

(86) PCT No.: PCT/US2004/011048

§ 371 (c)(1),
(2), (4) Date: Sep. 23, 2005

(87) PCT Pub. No.: WO2004/093946

PCT Pub. Date: Nov. 4, 2004

(65) Prior Publication Data

US 2006/0195061 A1  Aug. 31, 2006

(51) Int. Cl.
*A61N 5/00* (2006.01)
*A61M 29/00* (2006.01)
(52) U.S. Cl. .......................................... 600/5; 604/198
(58) Field of Classification Search ................. 600/1–8; 604/110, 192, 197, 198, 263; 250/506.1, 250/515.1; 128/919
See application file for complete search history.

(56) References Cited

U.S. PATENT DOCUMENTS

| 4,307,713 | A | 12/1981 | Galkin et al. |
| 4,743,233 | A | 5/1988 | Schneider |
| D313,470 | S | 1/1991 | Talonn et al. |
| 4,994,045 | A | 2/1991 | Ranford |
| 5,078,693 | A * | 1/1992 | Shine .................. 604/192 |
| 5,156,599 | A | 10/1992 | Ranford et al. |
| 5,163,916 | A | 11/1992 | Sunderland |
| D344,355 | S | 2/1994 | Talonn et al. |
| 5,403,287 | A | 4/1995 | Talonn et al. |
| 5,584,814 | A * | 12/1996 | Schuster et al. ............. 604/187 |
| 5,599,318 | A * | 2/1997 | Sweeney et al. ............ 604/263 |
| 6,162,198 | A | 12/2000 | Coffey et al. |
| 6,221,052 | B1 | 4/2001 | Caizza et al. |
| 6,368,303 | B1 | 4/2002 | Caizza |
| 6,432,087 | B1 | 8/2002 | Hoeck et al. |

OTHER PUBLICATIONS

Biodex Medical Systems: "Pro-Tec V Syringe Sheild", Available from the Internet, XP002293812, <http://www.biodex.com/radlo/syringes/syringes_737.htm>, Feb. 17, 2004.

* cited by examiner

*Primary Examiner*—Samuel G Gilbert

(57) ABSTRACT

A syringe injection shield (100) is formed primarily from a radio-opaque substance, such as tungsten, to shield medical personnel from exposure to radiation during administration of radiopharmaceuticals to patients. Safety syringes (22) typically have a needle sheath that can be positioned around a needle (24) after administration of the radiopharmaceutical. The syringe injection shield of the present invention allows medical personnel to make the syringe "safe" before the used syringe is removed from the syringe injection shield. The syringe is safe when the needle sheath is positioned and locked in place around the needle to reduce the risk of needle stick. The syringe injection shield includes a toggle element (110) that can assume four different positions as follows: neutral; ready; hold; and release.

20 Claims, 3 Drawing Sheets

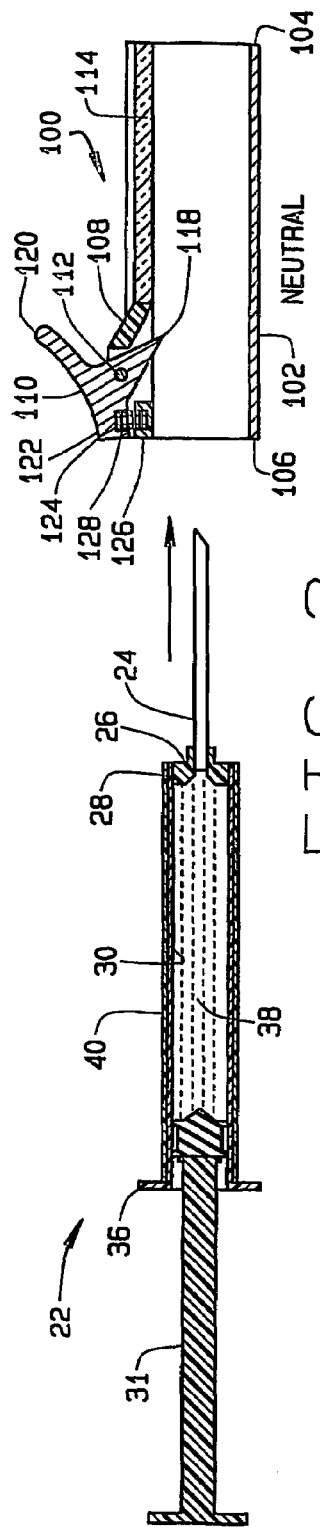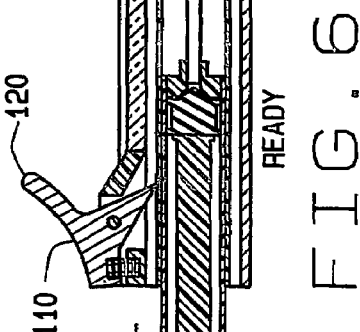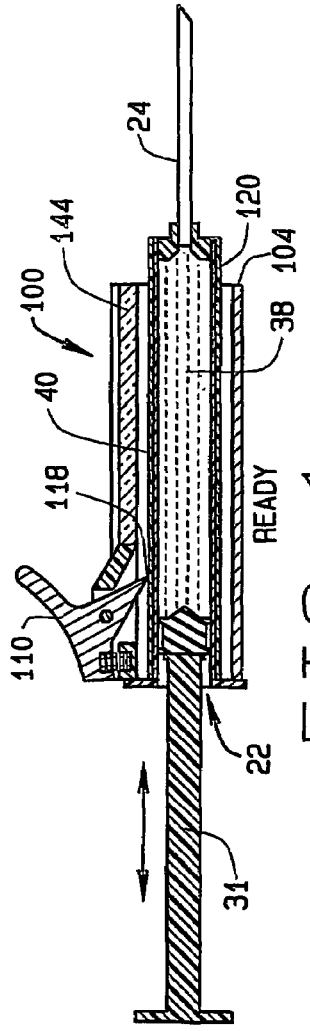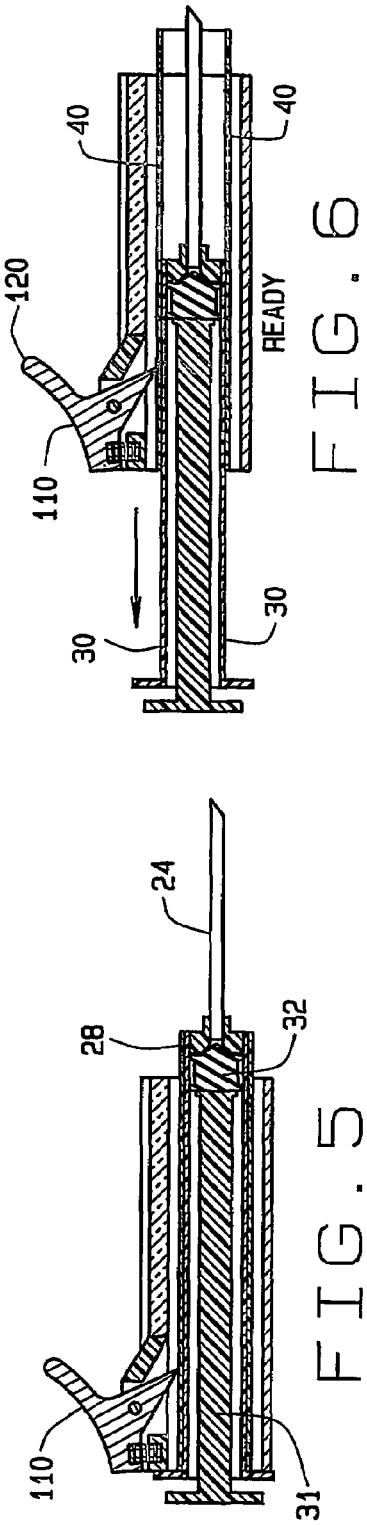
FIG. 3
FIG. 4
FIG. 5
FIG. 6

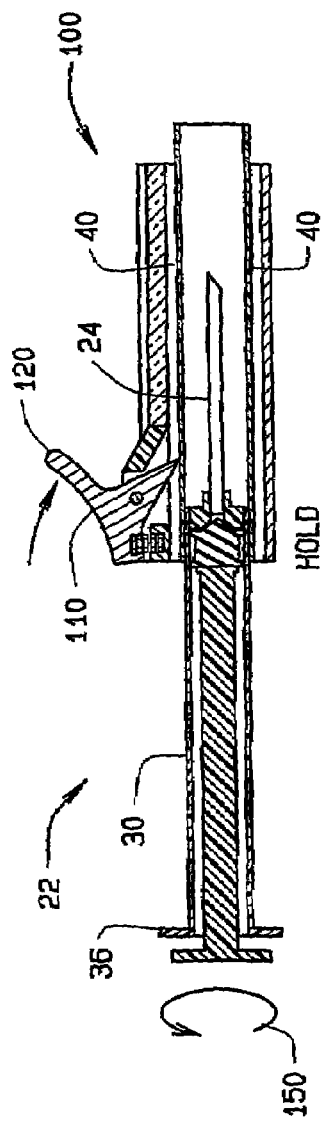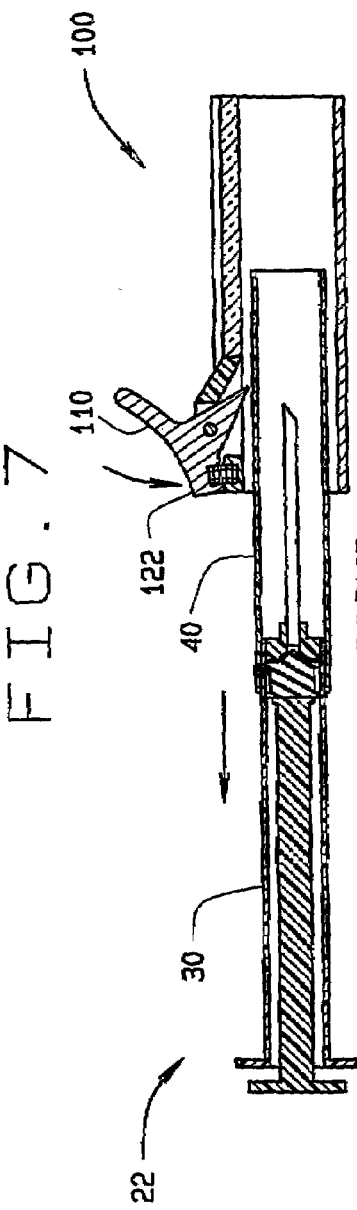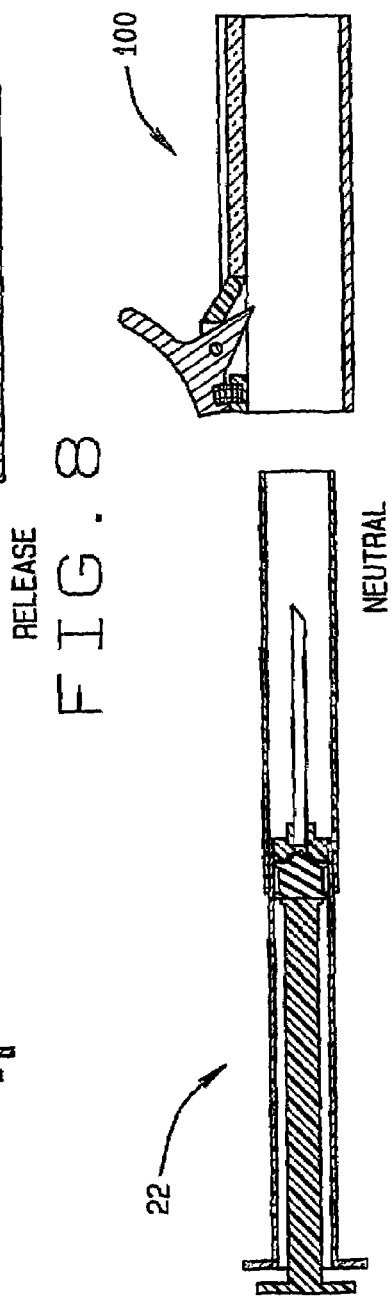

RADIATION SHIELD FOR A SAFETY SYRINGE HAVING A NEEDLE SHEATH

BACKGROUND OF INVENTION

Syringes, including those that are used to administer liquid radiopharmaceuticals pose a risk of needle stick. Various safety syringes have been developed to reduce the risk of needle stick, including the Monoject® sold by The Kendall Company, a business of Tyco International Ltd., having a place of business at 15 Hampshire St., Mansfield, Mass. and the SafetyLok® sold by Becton-Dickson and Company (B-D) having a place of business at 1 Becton Drive, Franklin Lakes, N.J. An illustrative example of the Monoject(E) type of technology includes that disclosed in U.S. Pat. No. 5,156,599 issued on Oct. 20, 1992, which is incorporated herein by reference. Illustrative examples of the Safety-Lok® technology include that disclosed in: U.S. Pat. No. 6,221,052, issued on Apr. 24, 2001, which is incorporated herein by reference; U.S. Pat. No. 6,432,087, issued on Aug. 13, 2002, which is incorporated herein by reference; and U.S. Pat. No. 6,368,303, issued on Apr. 9, 2002, which is incorporated herein by reference.

Both the Monoject® and the Safety-Lok® safety syringe have a cylindrical needle sheath that can be repositioned and locked after administration of a radiopharmaceutical to surround the needle to reduce the risk of needle stick.

Safety syringes with an extendable sheath design are also disclosed in: U.S. Pat. No. 4,994,045, issued to Ranford on Feb. 19, 1991, which is incorporated herein by reference; U.S. Pat. No. 4,998,924, issued to Ranford on Mar. 12, 1991, which is incorporated herein by reference; U.S. Pat. No. 4,743,233, issued to Schneider on May 10, 1988, which is incorporated herein by reference; U.S. Pat. No. 5,403,287, issued to Talonn et al. on Apr. 4, 1995, which is incorporated herein by reference; U.S. Pat. No. 5,163,916, issued to Sunderland on Nov. 17, 1992, which is incorporated herein by reference; U.S. Design Patent No. 313,470, issued to Talonn et al. on Jan. 1, 1991, which is incorporated herein by reference; and U.S. Design Patent No. 344,355, issued to Talonn et al. on Feb. 15, 1994, which is incorporated herein by reference.

The administration of radiopharmaceuticals can also pose a radiation exposure risk to medical personnel. The use of syringe injection shields reduces this risk. Biodex Medical Systems, Inc. of 20 Ramsay Rd., Shirley, N.Y. sells the Pro-Tec® II syringe injection shield. The Pro-Tec® II syringe injection shield uses tungsten shielding, a lead glass window and fits various disposable syringes. A thumbscrew holds the syringe in place.

Biodex also sells the Pro-Tec® III syringe injection shield. The Pro-Tec® III syringe injection shield is produced in two different models. One model is for regular syringes. The other model is designed to function with one or more safety syringes such as the Safety-Lok® sold by B-D or the Monoject® sold by The Kendall Company. There are two ways to remove a used safety syringe from the Pro-Tec® III syringe injection shield.

One approach is to invert the combination of syringe injection shield and used safety syringe so that the needle is pointing up relative to the floor. The release button is then pressed, allowing the used syringe to fall by gravity from the shield. Thereafter, the syringe is typically placed in a pharmaceutical pig (needle down) for transport to a nuclear pharmacy for disposal of the used safety syringe. Unfortunately, the needle remains exposed during the aforementioned disposal procedure. Approximately 50% of all needlesticks occur after injection and before disposal.

Another approach is to position the combination of syringe injection shield and used safety syringe so that the needle is pointing towards the floor. The release button is pressed, allowing the used syringe to be manually removed from the syringe injection shield. Thereafter, the syringe is typically placed in a pharmaceutical pig (needle down) for transport to a nuclear pharmacy for disposal of the used safety syringe. Unfortunately, the needle also remains exposed during the aforementioned disposal procedure. There is a need for a syringe injection shield that will allow a safety syringe to be placed in the "safe" position before the syringe is removed from the syringe injection shield. A safety syringe is in the safe position when the needle is covered by a sheath or other protective element and the sheath is locked in position relative to the needle.

There are various ways to place a safety syringe in the safe position, which is well known to those skilled in the art. For example, the Monoject® safety syringe is rotated to a locked position after the needle has been retracted into the needle sheath. The Safety-Lok® safety syringe uses a different locking procedure. First, the needle is retracted into the needle sheath, then the barrel is pulled longitudinally into a locked position. Other safety syringes that use different locking systems may be suitable for use with this invention.

The Pro-Tee® III syringe injection shield has a toggle element that can assume three positions, which are as follows: neutral; ready; and release. This prior art toggle element is in the neutral position when there is no syringe in the injection shield. The ready position for this prior art toggle element is when a syringe is in the injection shield. Finally, this prior art toggle element is in the release position when the syringe is being removed from the shield.

The prior art toggle element associated Pro-Tec® III syringe injection shield will not allow the syringe to be made safe prior to removal of the syringe from the shield due to the fact that this prior art toggle element cannot hold a syringe sheath in place so the sheath can be locked in position relative to the barrel and needle.

Many radiopharmaceuticals are injected into a patient's blood vessel. To confirm that the needle is properly positioned in the patient's blood vessel, medical personnel typically pull back on the syringe plunger to draw blood through the needle into the barrel of the syringe. If blood cannot be seen in the barrel of the syringe, the needle is repositioned and the process is repeated. The radiopharmaceutical is administered after the correct position of the needle has been confirmed by the presence of blood in the syringe barrel. For this reason, prior art syringe shields typically include a lead glass insert so medical personnel could attempt to see inside the barrel of the syringe while it was positioned in the syringe shield. Unfortunately, it is hard to see through the lead glass into the syringe barrel to confirm the presence of blood. There is a need for a syringe injection shield that allows easy visual confirmation of needle placement in a blood vessel. The present invention is directed to overcoming one or more of the problems set forth above.

SUMMARY OF INVENTION

The syringe injection shield of the present invention includes a generally tubular member that is sized to receive a safety syringe. The present invention is intended for use with various safety syringes including, but not limited to, the Monoject® safety syringe and the Safety-Lok® safety syringe. The tubular member of the present invention may be formed in different sizes to accommodate safety syringes from different sources. The tubular member is typically formed from tungsten or some other radio-opaque substance, which shields medical personnel from at least a portion of the radiation emitted from the radiopharmaceutical. A toggle housing is formed in the tubular member to support a movable toggle element. Unlike the prior art, the toggle element has four positions, which are as follows: a neutral position; a ready position; a hold position; and a release position. The toggle element forms a contact point that engages the needle sheath of a safety syringe when the toggle element is in the hold position. The toggle element allows medical personnel to make the safety syringe "safe" before the used syringe is removed from the syringe injection shield. In the preferred embodiment, the syringe injection shield of the present invention is slightly shorter than the safety syringe to make it easier to confirm proper placement of the needle in a blood vessel. However, in alternative embodiments, the length of the syringe injection shield could be flush with the end of the safety syringe. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which:

FIG. 3 is a section view of the syringe injection shield of FIG. 2 and the safety syringe prior to insertion of the safety syringe into the syringe injection shield. The toggle element is in the neutral position;

FIG. 4 is a section view of the syringe injection shield and safety syringe after the syringe has been inserted into the shield. The toggle element is now in the ready position. The needle is in the extended position and is exposed, prior to administration of the radiopharmaceutical to a patient;

FIG. 5 is a section view of the syringe injection shield and safety syringe of FIG. 4 after administration of the radiopharmaceutical. The needle is still in the extended position;

FIG. 6 is a section view of the safety syringe and syringe injection shield. The needle and syringe barrel are being moved from the extended position to the retracted position as shown by the arrow. The toggle element is still in the ready position;

FIG. 7 is a section view of the safety syringe and the syringe injection shield. The toggle element is in the hold position. The needle has been moved to the retracted position and the finger tabs and syringe barrel are being rotated as shown by the arrow to lock the needle sheath in place relative to the barrel. The syringe has been "made safe" after the needle has been moved from the extended to the retracted position and the barrel has been rotated and locked in place relative to the needle sheath;

FIG. 8 is a section view of the safety syringe and the syringe injection shield. The toggle element is in the release position. The safety syringe is being removed from the shield as indicated by the arrow. The safety syringe has been "made safe" prior to removal from the injection shield and the needle is protected by the needle sheath; and FIG. 9 is a section view of the syringe injection shield after the syringe has been removed. The safety syringe has been made safe and the toggle has returned to the neutral position.

DETAILED DESCRIPTION

Figure 1:
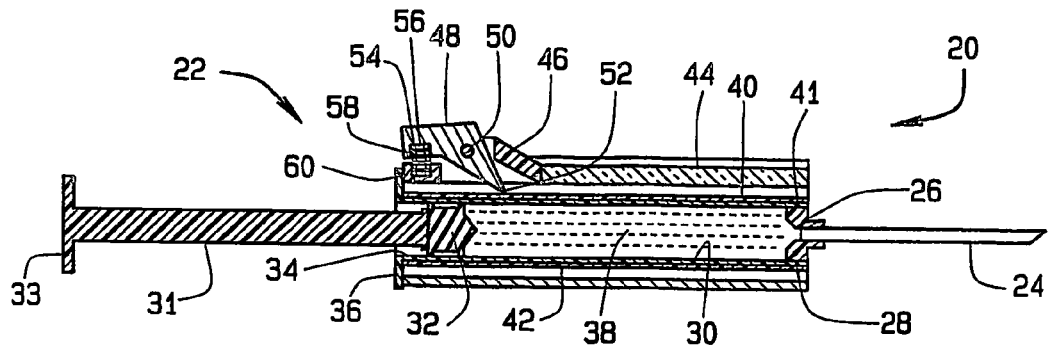
FIG. 1 is a section view of a safety syringe inserted into a prior art syringe injection shield.

FIG. 1 is a section view of a safety syringe inserted into a prior art syringe injection shield. The prior art syringe injection shield is generally identified by the numeral 20 and the safety syringe is generally identified by the numeral 22.

The safety syringe 22 has a needle 24, not shown to scale, that engages a luer lock 26, the exact configuration of which is well known to those skilled in the art. The luer lock 26 is positioned on one end 28 of the syringe barrel 30. A plunger 31 fits into the opposite end 34 of the barrel 30. An elastomeric seal 32 is positioned on one end of the plunger 31 and a push tab 33 is positioned on the opposite end. Finger tabs 36 are formed on the end 34 of the barrel 30, opposite the luer lock 26. The radiopharmaceutical 38 is contained inside the barrel 30 between the plunger 32 and the end 28.

A movable needle sheath 40 surrounds the barrel 30 and extends from the finger tabs 36 to the end 28. The barrel 30 and the needle 24 move relative to the needle sheath 40 as will be described below. A locking lug assembly 41 is positioned on the exterior of the end 28 of the barrel 30 and the interior of the needle sheath 40. Various locking lug assemblies known to those skilled in the art may be suitable for this purpose. To make the safety syringe 22 safe, the needle 24 is moved from the extended position, as shown in this figure to a retracted position, shown in subsequent figures and the barrel 30 is rotated relative to the needle sheath 40 to lock the needle sheath 40 in position surrounding the needle 24.

The syringe injection shield 20 includes a generally tubular member 42 that is formed from a radio-opaque material such as tungsten to reduce radiation exposure to medical personnel. A lead glass insert 44 is positioned in the tubular member 42. A toggle housing 46 supports a toggle element 48 that pivots on a shaft 50. The toggle element 48 defines a contact point 52 that engages the needle sheath 40. Opposite the contact point 52 is the release button 54. Below the release button is a recess 56 sized to receive one end of a spring 58. A portion 60 of the toggle housing 46 forms a spring receiver 61 that receives the opposite end of the spring 58. The spring 58 is under compression when positioned as shown in this figure, between the release button 54 of the toggle element 48 and the spring receiver 61. The purpose of the toggle element 48 in the prior art syringe injection shield 20 is to hold the safety syringe 22 in place during administration of the radiopharmaceutical. Unfortunately, the toggle element 48 of the prior art syringe injection shield 20 cannot hold the safety syringe 22 in place during rotation of the barrel 30 and therefore the safety syringe 22 cannot be made safe prior to withdrawal from the injection shield.

The toggle element 48 of this prior art injection shield 20 has the following three positions: neutral; ready; and release. In FIG. 1, the toggle element 48 is in the ready position. The contact point 52 is in contact with the needle sheath 40. When the release button 54 is depressed, the prior art toggle 48 is in the release position, not shown. In the release position, the contact point 52 is not in contact with the needle sheath 40. When there is no safety syringe 22 in the injection shield, this prior art toggle element 48 is in the neutral position.

Figure 2:
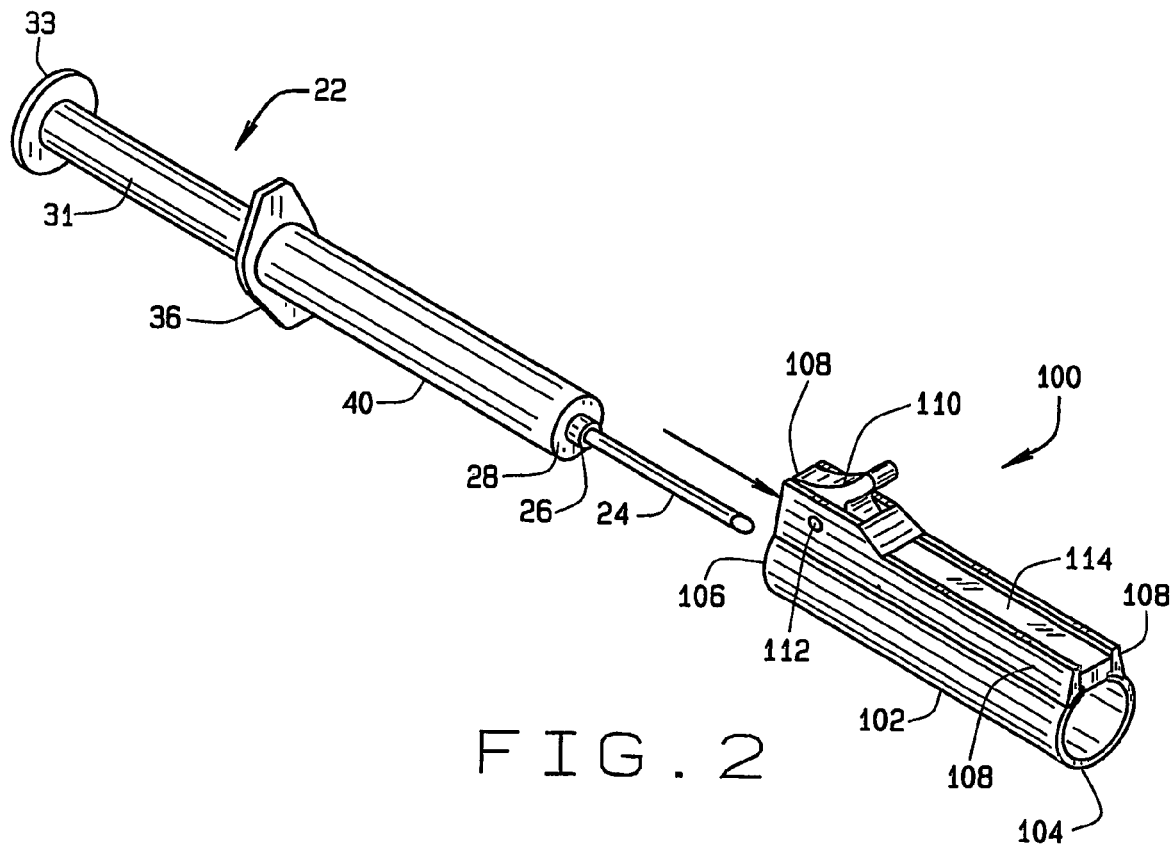
FIG. 2 is a perspective view of the syringe injection shield of the present invention and a safety syringe, prior to insertion of the safety syringe into the syringe injection shield.

FIG. 2 is a perspective view of the syringe injection shield of the present invention and a safety syringe 22, prior to insertion of the safety syringe 22 into a syringe injection shield. The syringe injection shield of the present invention is generally identified by the numeral 100. The syringe injection shield 100 includes a generally tubular member 102 that is formed from a radio-opaque material, such as but not limited to tungsten, to reduce radiation exposure to medical personnel from the radiopharmaceutical. The generally tubular member 102 is sized to receive the safety syringe 22. The tubular member has a distal end 104 and a proximal end 106.

A toggle housing 108 is mounted on the tubular member 102 and the toggle housing 108 is sized to receive a movable toggle element 110. A shaft 112 is mounted in the toggle housing 108 and the shaft 112 passes through the toggle element 110 allowing it to pivot inside the toggle housing 108. Unlike the prior art, the toggle element 110 of the present invention has four positions as follows: neutral; ready; hold; and release. Each of these four positions will be show in the following figures and discussed in sequential operational steps. A lead glass insert 114 is also positioned in the toggle housing 108.

FIG. 3 is a section view of the syringe injection shield 100 of FIG. 2 and the safety syringe 22 prior to insertion of the safety syringe 22 into the syringe injection shield 100. The toggle element 110 is in the neutral position. The toggle element 110 forms a contact point 118, an elongate tang 120 and a release tang 122. A recess 124 is formed beneath the release tang 122 and is sized to hold one end of the spring 128. A spring holder 126 is formed in a portion of the toggle housing 108 and is sized to hold the other end of the spring 128. When the spring 128 is in position as shown in this figure, the spring 128 is under compression urging the contact point 118 of the toggle element 110 into the neutral position. The radiopharmaceutical 38 has already been drawn into the barrel 30 of the safety syringe 22. To reduce radiation exposure to medical personnel during administration of the radiopharmaceutical to the patient, the loaded safety syringe 22 is first placed into the syringe injection shield 100 as shown in the next figure.

FIG. 4 is a section view of the syringe injection shield 100 and safety syringe 22 after the syringe has been inserted into the shield. The toggle element 110 is now in the ready position. The needle 24 is in the extended position and is exposed, prior to administration of the radiopharmaceutical 38 to a patient. In the ready position, the contact point 118 of the toggle element 110 engages the exterior surface of the needle sheath 40. As previously discussed, radiopharmaceuticals are often administered into the patient's blood vessel. To confirm proper placement of the needle 24 in the blood vessel, not shown, medical personnel pull back on the plunger 31 as indicated by the arrow to pull blood from the vessel through the needle into the barrel where the blood or the lack thereof can be observed by the medical personnel. The end 28 of the barrel 30 extends beyond the proximal end 106 of the syringe injection shield 100. To steady the syringe 100 for pullback, the finger tabs 36 are held in a fixed position relative to the syringe injection shield 100 by the medical personnel.

A portion 120 of the barrel 30 extends beyond the end 104 of the syringe shield 100. This extended portion 120 facilitates observation of the fluid in the barrel 30 by the medical personnel to confirm proper needle placement. This is easier and faster to see than peering through the dark lead glass 114 into the dark interior of the syringe shield 100. The extended portion 120 is exaggerated in the drawings to emphasize this feature. In the commercial embodiment, the length of the extension 120 is kept to a minimum to reduce radiation exposure. After confirmation of proper needle placement, the plunger 31 is fully depressed, as shown in the next figure, causing the radiopharmaceutical to flow from the barrel 30 through the needle 24 into the patient.

FIG. 5 is a section view of the syringe injection shield 100 and safety syringe 22 of FIG. 4 after administration of the radiopharmaceutical. The plunger 31 has been fully depressed and the seal 32 is in contact with the end 28 of the barrel 30.

FIG. 6 is a section view of the safety syringe 22 and the syringe injection shield 100 after the radiopharmaceutical has been administered to the patient. The needle 24 and barrel 30 have been moved from the extended position of FIGS. 4 and 5 to the retracted position of FIG. 7.

The toggle element 110 is then placed in the hold position as shown in this figure. In the hold position, pressure is applied by medical personnel to the elongate tang 120 of the toggle element 110 as indicated by the arrow so the contact point 118 will hold the needle sheath 40 in place relative to the injection shield while the finger tabs 36 and the barrel 30 are rotated as indicated by the arrow.

The amount of pressure needed on the toggle in the hold position can vary depending on the size of the elongate tang 120, the configuration of the contact point 118, the locking lug assembly 41 and the type of safety syringe 22. However, pressure from about 13 to about 20 pounds and more preferably from about 15 to about 18 pounds on the toggle has been sufficient to hold the needle sheath in place while the barrel is rotated and the syringe is made safe. Optimally, a pressure of about 16.5 pounds on the elongate tang will be sufficient while in the hold position.

FIG. 7 is a section view of the safety syringe 22 and the syringe injection shield 100. The toggle element 110 is in the hold position in this figure. In the hold position, pressure continues to be applied by medical personnel to the elongate tang 120 of the toggle element 110 as indicated by the arrow so the contact point 118 will hold the needle sheath 40 in place relative to the syringe barrel while the finger tabs 36 and syringe barrel 30 are being rotated as shown by the circular arrow 150 to properly engage the locking lug assembly 41, not shown. Locking lug assemblies are known in the art. In this figure, the needle 24 has been moved to the fully retracted position. The safety syringe 22 has been "made safe" after the needle 24 has been moved from the extended to the retracted position and the syringe barrel 30 has been rotated and locked in place relative to the needle sheath 40. When properly engaged, the locking lug assembly 41 prevents the needle 24 from being extended beyond the end of the needle sheath 40. The locked needle sheath 40 covers the needle 24 and reduces the risk of needle stick during disposal of the used safety syringe 22.

FIG. 8 is a section view of the safety syringe 22 and the syringe injection shield 100. The toggle element 110 is in the release position. In the release position, pressure is applied by medical personnel to the release tang 122 of the toggle element 110 as indicated by the arrow so the contact point 118 does not touch the needle sheath 40. The safety syringe is then removed from the shield for disposal. The safety syringe 22 has been "made safe" prior to removal from the syringe injection shield 100 and the needle 14 is protected by the needle sheath 40.

FIG. 9 is a section view of the syringe 22 and the syringe injection shield 100. The toggle element 110 is in the neutral position. The safety syringe 22 has been completely removed from the syringe injection shield 100 and is ready to be disposed. The needle 24 is protected by the needle sheath 40 and full use has been made of the features of the safety syringe 22.

The invention claimed is:

1. An injection shield assembly comprising:
   a generally tubular member sized to accommodate a needle sheath of a safety syringe, the member having a distal end and an opposing proximal end, the member comprising radiopaque material; and
   a movable toggle element designed to pivot relative to the member, the toggle element comprising:
      a first tang extending at least generally out away from an exterior of the injection shield assembly;
      a second tang disposed at least generally between the first tang and the proximal end of the member; and
      a third tang, at least a portion of which is located in a safety syringe accommodating aperture of the injection shield assembly.

2. An injection shield assembly as in claim 1, wherein the third tang is substantially tapered.

3. An injection shield assembly as in claim 1, wherein the member comprises a toggle housing, and the toggle element designed to pivot relative to the toggle housing.

4. An injection shield assembly as in claim 3, further comprising a spring disposed between the toggle housing and the toggle element.

5. An injection shield assembly as in claim 4, further comprising a shaft mounted to the toggle housing and passing through the toggle element, the toggle element being designed to pivot about the shaft.

6. An injection shield assembly as in claim 5, wherein the spring is spaced from and does not contact the shaft.

7. An injection shield assembly as in claim 3, further comprising a lead glass insert positioned in the toggle housing.

8. An injection shield assembly as in claim 1, further comprising a shaft about which the toggle element is designed to pivot, wherein the first tang extends away from the shaft in a first direction, the second tang extends away from the shaft in a second direction, and the third tang extends away from the shaft in a third direction.

9. An injection shield assembly as in claim 1 further comprising a safety syringe having a barrel, a needle, a plunger, and a needle sheath, wherein the needle sheath is disposed about and movable relative to the barrel, and wherein
   the member is disposed about at least a portion of the needle sheath.

10. An injection shield assembly as in claim 9, wherein the third tang is in contact with the needle sheath.

11. An injection shield assembly as in claim 10, wherein a length of the member is shorter than a length of the barrel.

12. A method of using an injection shield assembly, the method comprising:
    inserting a safety syringe into an injection shield in a manner such that the injection shield is disposed about a needle sheath of the safety syringe;
    changing a condition of the safety syringe from a first condition in which a needle of the safety syringe is exposed for use, to a second condition in which the needle sheath is substantially disposed about the needle, wherein the changing is accomplished while the injection shield is disposed about the needle sheath, and the changing comprises applying pressure to a first tang of a toggle element of the injection shield; and
    removing the safety syringe from the injection shield, wherein the removing comprises applying pressure to a second tang of the toggle element.

13. A method as in claim 12, wherein the disposing comprises contacting the needle sheath with the toggle element of the injection shield.

14. A method as in claim 12, wherein the changing comprises contacting the needle sheath with the toggle element of the injection shield.

15. A method as in claim 14, wherein the contacting comprises holding the needle sheath in place relative to the injection shield while a barrel of the safety syringe is rotated relative thereto.

16. A method as in claim 12, wherein the toggle element does not touch the safety syringe during the removing.

17. A method as in claim 12, wherein the changing comprises supplementing the pressure applied to the toggle element with a spring force.

18. A method as in claim 12, wherein the removing comprises imposing a spring force on the second tang in a direction substantially opposite that of the pressure applied.

19. An injection shield assembly comprising:
    a safety syringe having a barrel, a needle, a plunger, and a needle sheath, wherein the needle sheath is disposed about and movable relative to the barrel; and
    an injection shield comprising:
       a generally tubular member comprising radiopaque material and disposed about at least a portion of the needle sheath of the safety syringe; and
       a movable toggle element designed to pivot about a shaft of the injection shield relative to the generally tubular member, the toggle element comprising:
          a first tang that extends away from the shaft in a first direction;
          a second tang that extends away from the shaft in a second direction; and
          a contact point that extends away from the shaft in a third direction, the contact point being designed to be moved in and out of contact with the needle sheath of the safety syringe.

20. An injection shield assembly as in claim 19, further comprising a spring that biases the first tang at least generally toward the needle sheath and that biases the second tang at least generally away from the needle sheath.

* * * * *